United States Patent [19]

Bharucha et al.

[11] 4,264,617

[45] * Apr. 28, 1981

[54] ANTIVIRAL 5-(SUBSTITUTED BENZAL) HYDANTOINS

[75] Inventors: Kekhusroo R. Bharucha, Toronto; Djordje Ajdukovic, Montreal; Vytautas Pavilanis, Westmount; Heinrich M. Schrenk, Don Mills, all of Canada

[73] Assignees: Canada Packers, Limited, Toronto; The Institute of Microbiology and Hygiene of the University of Montreal, Ville Laval, both of Canada

[*] Notice: The portion of the term of this patent subsequent to Mar. 22, 1994, has been disclaimed.

[21] Appl. No.: 909,565

[22] Filed: May 25, 1978

Related U.S. Application Data

[60] Division of Ser. No. 640,166, Dec. 12, 1975, which is a division of Ser. No. 478,310, Jun. 11, 1974, Pat. No. 4,013,770, which is a continuation-in-part of Ser. No. 262,920, Jun. 16, 1972, abandoned.

[51] Int. Cl.$^3$ ............................................. A61K 31/415
[52] U.S. Cl. ................................................. 424/273 R
[58] Field of Search ..................................... 424/273 R

[56] References Cited

PUBLICATIONS

Deulofeu et al., Z. Physiol. Chem. 219, pp. 233 to end (1933).

*Primary Examiner*—Jerome D. Goldberg
*Attorney, Agent, or Firm*—Bacon & Thomas

[57] ABSTRACT

Therapeutic compositions containing a compound of the formula:

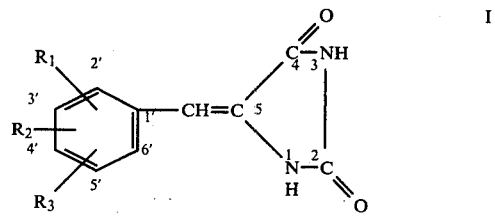

wherein:

$R_1$, $R_2$, and $R_3$ are each hydrogen, hydroxy, alkoxy of 1 to 4 carbon atoms, acyloxy of 1 to 4 carbon atoms, halo, or nitro, or $R_2$ and $R_3$ together form —OCH$_2$O—; or the corresponding acylated derivatives wherein there are one or more acyl groups in the hydantoin moiety and each acyl group contains from 1 to 20 carbon atoms, and the use of said compounds to control virus infections, in particular those caused by entero and foot and mouth disease viruses of the Picorna group.

16 Claims, No Drawings

ANTIVIRAL 5-(SUBSTITUTED BENZAL) HYDANTOINS

COPENDING APPLICATIONS

This application is a division of Application Ser. No. 640,166, filed Dec. 12, 1975, which application is a division of Application Ser. No. 478,310, filed June 11, 1974 and now issued as U.S. Pat. No. 4,013,770, which application Ser. No. 478,310 is in turn a continuation-in-part of Application Ser. No. 262,920, filed June 16, 1972, now abandoned. The present application is also related to Application Ser. No. 640,167, filed Dec. 12, 1975 and issued as U.S. Pat. No. 4,065,570 and to Application Ser. No. 640,168, filed Dec. 12, 1975 and issued as U.S. Pat. No. 4,065,571. The aforesaid Applications Ser. Nos. 640,167 and 640,168 were divisions of Ser. No. 478,310 filed June 11, 1974 as a continuation-in-part of Ser. No. 262,920 filed June 16, 1972.

The present invention relates to a series of 5-(substituted benzal) hydantoins and their acylated derivatives, and their use as antiviral agents. The compounds described herein have been found to be particularly effective against the Picorna group of viruses.

The invention, in particular, relates to therapeutic compositions containing a compound of the formula:

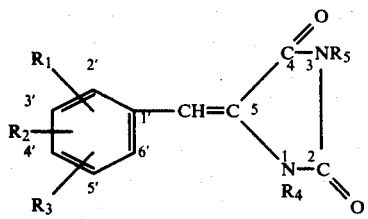

wherein:

$R_1$, $R_2$ and $R_3$ are each hydrogen, hydroxy, alkoxy of 1 to 4 carbon atoms, acyloxy of 1 to 4 carbon atoms, halo, or nitro or $R_2$ and $R_3$ together form —OCH$_2$O—; and $R_4$ and $R_5$ are each hydrogen or acyl groups containing from 1 to 20 carbon atoms, and the use of said compounds to control virus infections, in particular those caused by entero and foot and mouth disease viruses of the Picorna group. It will be understood that the formula I is intended to include geometrical isomers and mixtures thereof.

Various 5-(substituted benzal) hydantoins and their preparation have been described in the prior art. See for example U.S. Pat. Nos. 2,605,282; 2,861,079; and 2,479,065, as well as German Pat. No. 1,030,050; Deulofeu and Mendivelzua, Z. physiol. Chem., 219, 233 (1933), and G. Billek, Monatsh. Chem., 92, 352 (1961).

It has now been unexpectedly and surprisingly discovered that certain 5-(substituted benzal) hydantoins having the formula I exhibit antiviral activity, especially against the Picorna group of viruses.

The present invention therefore also provides a method for controlling an infection caused by a virus of the Picorna group in a vertebrate which comprises administering to a susceptible or infected vertebrate an effective but non-toxic amount of a compound of the formula I or an acylated derivative thereof as defined above.

A preferred group of compounds is those compounds of the formula I or their acylated derivatives wherein $R_1$ is —OCH$_3$ or hydrogen, and $R_2$ and $R_3$ are —OCH$_3$. Especially preferred are compounds where $R_1$ is hydrogen, $R_2$ is 3'—OCH$_3$ and $R_3$ is 4'—OCH$_3$; and their acetylated and propionated derivatives.

The therapeutic compositions of the invention comprise the herein described compounds and a pharmaceutical carrier.

The compounds may be used individually or in the form of mixed isomers, both geometrical and positional, and mixed mono- and di-acylated derivatives thereof such as obtained in a crude reaction mixture. Very suitable mixtures of this type are the acetylated derivatives prepared by reacting a compound of the formula I with acetic anhydride with or without anhydrous sodium acetate, or by acetylating the compound with acetic anhydride or with an acetyl halide in a suitable dipolar aprotic solvent, such as dimethylacetamide in the presence of an organic base, e.g. pyridine.

One method for preparing the unacylated 5-(substituted benzal) hydantoins is that of E. C. Britton and H. T. Smith, U.S. Pat. No. 2,861,079. Alternatively, the method described in U.S. Pat. No. 2,605,282 can be used, as well as the method of Wheeler and Hoffman, American Chemical Journal, 45, 368 (1911).

In the method of E. C. Britton and H. T. Smith, the appropriately substituted benzaldehyde is heated with hydantoin in the presence of a monoalkanolamine. When the reaction is complete (ca. 4 hours), the reaction mixture is acidified with dilute mineral acid, such as hydrochloric acid, cooled and filtered. The 5-(substituted benzal) hydantoin is then dried and, if desired, may be purified by crystallization from a suitable solvent.

The unacetylated compound can also be obtained by saponification of the acetylated material prepared as described below.

The acylated derivatives of the herein described 5-(substituted benzal) hydantoins can be prepared by various routes.

We have found that the 5-(substituted benzal) hydantoins are quite insoluble in the usual organic solvents and this makes acetylation or acylation quite difficult. However, by using a dipolar aprotic solvent, such as dimethylacetamide or dimethylformamide, the 5-(substituted benzal) hydantoins can be readily dissolved and in such solution can be acylated by conventional acylating agents such as alkanoyl halides, e.g., acetyl chloride, pivaloyl chloride, palmitoyl chloride or acid anhydrides, e.g., acetic anhydride, in the presence of a base such as pyridine.

It was previously reported by Deulofeu and Mendivelzua, Z. physiol, Chem. 219, 233 (1933) that the condensation of veratraldehyde (3,4-dimethoxybenzaldehyde) with hydantoin in acetic anhydride in the presence of fused anhydrous sodium acetate gave 5-(3',4'-dimethoxybenzal) hydantoin. We have now found, however, that this reaction leads to the formation of a corresponding acetylated product.

As mentioned hereinabove, the compounds of the present invention exhibit antiviral activity against the Picorna group of viruses. It has been found, however, that the degree of antiviral activity dramatically increases upon acylation of the 5-(substituted benzal) hydantoins in the hydantoin moiety. Thus in the condensation of 3,4-dimethoxybenzaldehyde with hydantoin by the method of Deulofeu and Mendivelzua (loc. cit.) the acetylated-5-(3',4'-dimethoxybenzal) hydantoin was found to have a greater degree of antiviral activity than the unacetylated compound, 5-(3',4'-dimethoxybenzal) hydantoin.

Similarly, the other acylated-5-(substituted benzal) hydantoins can be prepared by heating the appropriately substituted benzaldehyde and an anhydrous alkali metal alkanoate together with hydantoin and the corresponding acid anhydride. The reaction is generally conducted at an elevated temperature until the reaction is substantially complete. For example, in the reaction of benzaldehydes with hydantoin in the presence of anhydrous sodium acetate and acetic anhydride, the reaction is generally carried out at about 125°–140° C. it has also been found that potassium bicarbonate can be used in place of the anhydrous alkali metal alkanoate with similar results being obtained. After the condensation is complete, the reaction mixture is cooled, usually overnight, treated with water and then refrigerated for several hours. The crystalline product is then filtered, washed with water and dried. The major portion of the product appears to be the mono-acylated compound, together with small amounts of di-acylated compound. Where the aromatic aldehyde starting material contains phenolic hydroxylic groups, it has been found that these are acylated under the conditions of the reaction. Thus protocatechualdehyde, hydantoin, anhydrous sodium acetate, and acetic anhydride gave acetylated 5-(3',4'-diacetoxybenzal) hydantoin.

As mentioned above, the acylated derivatives of the herein described hydantoins exhibit a higher degree of antiviral activity than that of the unacylated compounds.

It has been found that further acylation of the acylated product obtained by the condensation of the aromatic aldehyde and hydantoin in the presence of the alkanoate salt affords a product having greater antiviral activity than that of the starting material. The further acylation is generally carried out with the appropriate acid anhydride. Thus refluxing the acetylated 5-(3',4'-dimethoxybenzal) hydantoin obtained by the condensation of 3,4-dimethoxybenzaldehyde with hydantoin as described above, in acetic anhydride for about 5 hours gave a product having enhanced antiviral activity as compared to the starting material.

It has been found also that reaction of the 5-(substituted benzal) hydantoin, prepared either by the method of Britton and Smith (loc. cit.) or by saponification of the product obtained in the condensation of the aromatic aldehyde and hydantoin, in refluxing acid anhydride for several hours affords an acylated product having enhanced antiviral activity.

Notwithstanding this increase in antiviral behavior, it has also been discovered that reaction of the 5-(substituted benzal) hydantoin with the appropriate anhydrous alkali metal alkanoate and acid anhydride affords an acylated product having an even higher degree of antiviral activity. Thus, the reaction of 5-(3',4'-dimethoxybenzal) hydantoin with anhydrous sodium acetate and acetic anhydride for about ½ hour at 125°–130° C. (bath temperature) gave an acetylated 5-(3',4'-dimethoxybenzal) hydantoin having exceptionally good antiviral activity.

Although the reasons for this behavior is not yet definitely known, in examining the general structural formuall of the 5-(substituted benzal) hydantoins of the invention, it will be realized that the acylation can occur in the 1- and 3-positions of the hydantoin moiety. It is believed that the degree of antiviral activity of the hydantoins may be dependent upon the location and degree of acylation, as well as the geometrical configuration of the compound. For example, in the case of acetylation of 5-(3',4'-dimethoxybenzal) hydantoin carried out with refluxing acetic anhydride the crude acetylated product is separable into pure N-mono- and N,N-diacetylated derivatives. In tissue culture tests the latter showed much greater anti-viral activity than the former which, in turn, was more active than the unacetylated compound. It will be further appreciated by those skilled in the art that the hydantoin moiety is capable of keto-enol tautomerism, and consequently the acylation may provide some O-acylation, as well as N-acylation. All of the products of acylation are to be considered within the scope of the present invention.

The presence of the double bond between the carbon atom of the hydantoin ring and the α-carbon of the benzal moiety creates the possibility of cis-trans isomerism. It will be understood that the invention embraces both isomeric forms of the herein described 5-(substituted benzal) hydantoin compounds and of their acylated derivatives, individually, as well as mixtures of the isomers. In the case of the acylated compounds the invention embraces the mono and diacylates, individually as well as in the form of mixtures.

The mixtures may be separated into the pure compounds by fractional crystallizations from dipolar aprotic solvents such as dimethylsulfoxide and dimethylacetamide. For example, the mono- and di-acetates as well as their positional and geometric isomers may be separated by this means.

As mentioned hereinabove, the benzaldehydes used in carrying out the process described herein may carry various substituents, such as hydroxy, alkoxy, acyloxy, halo (viz. fluoro, chloro, and bromo), nitro and methylenedioxy. Particularly preferred substituent are alkoxy groups of up to four carbons, in particular, methoxy groups. It has been found that outstanding activity against Picorna group of viruses is obtained with di- and tri-methoxy benzal hydantoins. Especially preferred compounds are the 5-(3',4'-dimethoxybenzal)- and 5-(2',4',5'-trimethoxybenzal) hydantoins and their acylated derivatives.

The compounds of the present invention have been found to be highly effective against the Picorna group of viruses. The Picorna viruses are a group of small RNA viruses comprising enteroviruses (poliomyelitis, coxsackie, and endo viruses), rhinoviruses, and viruses of non-human origin such as foot-and-mouth virus of cattle. The outstanding characteristics of the compounds of the present invention are their high degree of inhibition against the above viruses, even at concentrations below 1 µg/ml, coupled with their low order of toxicity.

The in vitro activity of representative compounds of the present invention are set forth below.

In preparing the compounds for testing, they were handled aseptically throughout. The compounds were dissolved in a minimum amount of a suitable solvent, and the final dilutions were made up to the required volume in a complete culture medium in a concentration not exceeding the predetermined maximum non-cytotoxic levels. All materials were tested by weight, first at three concentrations, 100-10-1 µg/ml and those which showed an inhibiting activity in that range were carefully retested at several concentrations below the maximum non-cytotoxic level.

The cell cultures used in all primary in vitro antipicorna virus screening tests were an established cell line of the African green monkey kidney (VERO), a primary cell culture of the Cercopythecus monkey kidney, or human embryonic lung diploid cells WI-38.

The cytotoxic studies were performed on each of the compounds to determine the level of response of the cells used to the potentially toxic action of the substances. Cytotoxic levels were expressed as a 50% inhibition of the cell growth as compared to the appropriate controls ($CTD_{50}$) or as a maximal non-toxic concentration ($CTD_0$) which does not produce any morphologically detectable inhibition of cell growth.

Standard batches of the viruses were made by growing the virus in an appropriate cell culture and then making a pool which was dispersed in ampoules and kept frozen at −76° C. until used. The titer of each virus was determined in the cell cultures used.

The cells were grown in test tubes in a suitable medium. Immediately before use the initial medium was replaced with the one which contained the test compound in an appropriate concentration. After the virus was added, the infected culture was incubated at 37° C. for a number of days and the cytopathic effect of the virus observed and recorded. The results were read every day in all of the tubes and the destruction of cells assessed in percentage of the cell sheet destroyed: 0-2-5-50-75-100%. As controls, cells with only virus (for cytopathic effect) or with only the compound (for cytotoxic effect) were used as well as the normal, uninfected cells (no cytotoxic-no cytopathic effects).

Degree of a specific cytopathic effect or its inhibition was calculated at the time when the cell virus-control tubes showed complete destruction of the cell monolayer sheet. Net difference in cytopathic effect between treated and control tubes expressed in percentage give the extent of the inhibitory activity of the substance. From these data a dose-response curve was then calculated and plotted.

The $TCID_{50}$ represents the tissue culture infective dose of virus that will destory 50 percent of the cells.

5-(3',4'-DIMETHOXYBENZAL) HYDANTOIN

| Polio I. Primary Monkey Cells; 316 $TCID_{50}$ | |
|---|---|
| Concentration of Compound | % Inhibition |
| 100 micrograms/ml | 45 |
| 50 micrograms/ml | 34 |

ACETYLATED 5-(3',4'-DIMETHOXYBENZAL) HYDANTOIN (A) Prepared according to the method of Deulofeu and Mendivelzua (loc. cit.) (Example 14)

| Polio I, Vero Cells; 316 $TCID_{50}$ | |
|---|---|
| Concentration of Compound | % Inhibition |
| 10 micrograms/ml | 100 |
| 5 micrograms/ml | 100 |
| 1 micrograms/ml | 100 |
| 0.5 micrograms/ml | 93 |

| Coxsackie $B_3$, Vero Cells; 173 $TCID_{50}$ | |
|---|---|
| Concentration of Compound | % Inhibition |
| 10 micrograms/ml | 100 |
| 5 micrograms/ml | 100 |
| 1 micrograms/ml | 97 |
| 0.5 micrograms/ml | 88 |

| Echo 9, Vero Cells; 31.6 $TCID_{50}$ | | | |
|---|---|---|---|
| Cytotoxicity | | Concentration | |
| $CTD_{50}$ (μg/ml) | $CTD_0$ (μg/ml) | of Compound (μg/ml) | % Inhibition |
| >100 | >10 | 10.0 | 100 |
| | | 6.7 | 100 |
| | | 3.3 | 92 |
| | | 1.0 | 71 |
| | | 0.7 | 42 |
| | | 0.3 | 29 |
| | | 0.1 | 8 |

| Echo 11, Primary Monkey Kidney Cells, 179 $TCID_{50}$ | | | |
|---|---|---|---|
| Cytotoxicity | | Concentration | |
| $CTD_{50}$ (μg/ml) | $CTD_0$ (μg/ml) | of Compound (μg/ml) | % Inhibition |
| >100 | >100 | 100 | 100 |
| | | 50 | 100 |
| | | 25 | 100 |
| | | 10 | 100 |
| | | 6.7 | 100 |
| | | 3.3 | 100 |
| | | 1.0 | 68 |
| | | 0.7 | 32 |
| | | 0.3 | 32 |
| | | 0.1 | 7 |

| Rhino 2, WI-38 Cells, 316 $TCID_{50}$ | | | |
|---|---|---|---|
| Cytotoxicity | | Concentration | |
| $CTD_{50}$ (μg/ml) | $CTD_0$ (μg/ml) | of Compound (μg/ml) | % Inhibition |
| >101 | >100 | 10 | 100 |
| | | 6.7 | 100 |
| | | 3.3 | 100 |
| | | 1.0 | 71 |
| | | 0.7 | 43 |
| | | 0.3 | 32 |
| | | 0.1 | 12 |

(B) Prepared by acetylation of 5-(3',4'-dimethoxybenzal) hydantoin with acetic anhydride.

| Coxsackie $B_3$, Vero Cells; 562 $TCID_{50}$ | |
|---|---|
| Concentration of Compound | % Inhibition |
| 1.0 micrograms/ml | 100 |
| 0.5 micrograms/ml | 95 |
| 0.1 micrograms/ml | 75 |
| 0.05 micrograms/ml | 50 |
| 0.01 micrograms/ml | 20 |

(C) Prepared by acetylation of 5-(3',4'-dimethoxybenzal) hydantoin with sodium acetate-acetic anhydride.

| Concentration of Compound | % Inhibition |
|---|---|
| 1.0 micrograms/ml | 100 |
| 0.5 micrograms/ml | 100 |
| 0.1 "100 | |
| 0.05 micrograms/ml | 50 |
| 0.01 micrograms/ml | 25 |

ACETYLATED 5-(3'-METHOXY-4'-ACETOXYBENZAL) HYDANTOIN (EXAMPLE 15)

| Polio I, Vero Cells; 56.2 $TCID_{50}$ | |
|---|---|
| Cytotoxicity | Concentration |

-continued

| CTD$_{50}$ (μg/ml) | CTD$_0$ (μg/ml) | of Compound (μg/ml) | % Inhibition |
|---|---|---|---|
| >100 | >10 | 10 | 100 |
|  |  | 5 | 100 |
|  |  | 1 | 12 |
|  |  | 0.5 | 19 |
|  |  | 0.1 | 7 |

Coxsackie B$_3$, Vero Cells; 562 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| >100 | >10 | 10 | 80 |
|  |  | 5 | 60 |
|  |  | 1 | 4 |

ACETYLATED 5-(DENZAL) HYDANTOIN
(EXAMPLE 16)

Polio I, Vero Cells; 56.2 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| 83 | 10 | 10 | 19 |
|  |  | 5 | 0 |
|  |  | 1 | 0 |

Coxsackie B$_3$, Vero Cells; 562 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| 83 | 10 | 10 | 25 |
|  |  | 5 | 0 |
|  |  | 1 | 0 |

ACETYLATED 5-(2',4',5'-TRIMETHOXYBENZAL) HYDANTOIN
(EXAMPLE 22)

Polio I, Vero Cells; 100 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
|  |  | 1 | 100 |
|  |  | 0.7 | 93 |
|  |  | 0.3 | 90 |
|  |  | 0.1 | 50 |
|  |  | 0.07 | 25 |
|  |  | 0.03 | 0 |
|  |  | 0.01 | 0 |

Polio I, Vero Cells; 10 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
|  |  | 1 | 100 |
|  |  | 0.7 | 98 |
|  |  | 0.3 | 98 |
|  |  | 0.1 | 54 |
|  |  | 0.07 | 27 |
|  |  | 0.03 | 8 |
|  |  | 0.01 | 4 |

Coxsackie B$_3$, Vero Cells; 178 TCID$_{50}$

| Cytotoxicity | | Concentration | |
|---|---|---|---|
| CTD$_{50}$ | CTD$_0$ | of Compound | |

-continued

| (μg/ml) | (μg/ml) | (μg/ml) | % Inhibition |
|---|---|---|---|
| >100 | 1 | 1 | 90 |
|  |  | 0.7 | 88 |
|  |  | 0.3 | 75 |
|  |  | 0.1 | 50 |
|  |  | 0.07 | 37 |
|  |  | 0.03 | 12 |
|  |  | 0.01 | 0 |

2 Coxsackie B$_3$, Vero Cells; 56.2 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| >100 | 1 | 1 | 100 |
|  |  | 0.7 | 97 |
|  |  | 0.3 | 90 |
|  |  | 0.1 | 50 |
|  |  | 0.07 | 43 |
|  |  | 0.03 | 37 |
|  |  | 0.01 | 19 |

ACETYLATED 5-(3',4',5'-TRIMETHOXYBENZAL) HYDANTOIN
(EXAMPLE 23)

Polio I, Vero Cells; 316 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| 50 | 10 | 10 | 96 |
|  |  | 6.7 | 72 |
|  |  | 3.3 | 56 |
|  |  | 1 | 46 |
|  |  | 0.7 | 36 |
|  |  | 0.3 | 14 |
|  |  | 0.1 | 0 |

Polio I, Vero Cells; 17.8 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| 50 | 10 | 10 | 100 |
|  |  | 6.7 | 95 |
|  |  | 3.3 | 60 |
|  |  | 1 | 56 |
|  |  | 0.7 | 42 |
|  |  | 0.3 | 32 |
|  |  | 0.1 | 21 |

Coxsackie B$_3$, Vero Cells, 316 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| 50 | 10 | 10 | 97 |
|  |  | 6.7 | 93 |
|  |  | 3.3 | 88 |
|  |  | 1.0 | 68 |
|  |  | 0.7 | 25 |
|  |  | 0.3 | 0 |
|  |  | 0.1 | 0 |

Coxsackie B$_3$, Vero Cells, 178 TCID$_{50}$

| Cytotoxicity | | Concentration | |
|---|---|---|---|
| CTD$_{50}$ (μg/ml) | CTD$_0$ (μg/ml) | Of Compound (μg/ml) | % Inhibition |
| 50 | 10 | 10 | 100 |
|  |  | 6.7 | 100 |
|  |  | 3.3 | 100 |
|  |  | 1.0 | 88 |
|  |  | 0.7 | 62 |
|  |  | 0.3 | 25 |

| | |
|---|---|
| 0.1 | 12 |

ACETYLATED 5-(3',5'-DIMETHOXYBENZAL) HYDANTOIN
(EXAMPLE 21)

32 Polio I, Vero Cells; 100 TCID$_{50}$

| Cytotoxicity | | Concentration | |
|---|---|---|---|
| CTD$_{50}$ (μ/ml) | CTD$_0$ (μg/ml) | of Compound (μg/ml) | % Inhibition |
| >100 | 100 | 10 | 100 |
| | | 5 | 100 |
| | | 1 | 32 |
| | | 0.5 | 0 |

Polio I, Vero Cells; 10 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| >100 | 100 | 10 | 100 |
| | | 5 | 100 |
| | | 1 | 50 |
| | | 0.5 | 15 |

Coxsackie B$_3$, Vero Cells; 316 TCID$_{50}$

| Cytotoxicity | | Concentration | |
|---|---|---|---|
| CTD$_{50}$ (μg/ml) | CTD$_0$ (μg/ml) | Of Compound (μg/ml) | % Inhibition |
| 100 | 100 | 10 | 100 |
| | | 5 | 100 |
| | | 1 | 50 |
| | | 0.5 | 25 |

Coxsackie B$_3$, Vero Cells; 17.8 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| 100 | 100 | 10 | 100 |
| | | 5 | 99 |
| | | 1 | 44 |
| | | 0.5 | 21 |

PURE N-MONOACETYLATED 5-(3',4'-DIMETHOXYBENZAL) HYDANTOIN
(EXAMPLE 31)

Coxsackie B$_3$, Vero Cells; 1000 TCID$_{50}$

| Cytotoxicity | | Concentration | |
|---|---|---|---|
| CTD$_{50}$ (μg/ml) | CTD$_0$ (μg/ml) | Of Compound (μg/ml) | % Inhibition |
| 100 | 10 | 50 | 25 |
| | | 10 | 7 |
| | | 5 | 0 |
| | | 1 | 0 |

Coxsackie B$_3$, Vero Cells; 100 TCID$_{50}$

| Cytotoxicity | | Concentration | |
|---|---|---|---|
| CTD$_{50}$ (μg/ml) | CTD$_0$ (μg/ml) | Of Compound (μg/ml) | % Inhibition |
| 100 | 10 | 50 | 56 |
| | | 10 | 25 |
| | | 5 | 0 |
| | | 1 | 0 |

Polio I, Vero Cells; 316 TCID$_{50}$

| Cytotoxicity | | Concentration | |
|---|---|---|---|
| CTD$_{50}$ (μg/ml) | CTD$_0$ (μg/ml) | Of Compound (μg/ml) | % Inhibition |
| 100 | 10 | 50 | 84 |
| | | 10 | 7 |
| | | 5 | 0 |
| | | 1 | 0 |

PURE N,N-DIACETYLATED 5-(3'4'-DIMETHOXYBENZAL) HYDANTOIN
(EXAMPLE 32)

Coxsackie B$_3$, Vero Cells; 1000 TCID$_{50}$

| Cytotoxicity | | Concentration | |
|---|---|---|---|
| CTD$_{50}$ (μg/ml) | CTD$_0$ (μg/ml) | Of Compound (μg/ml) | % Inhibition |
| 33 | 10 | 50 | 100 |
| | | 10 | 100 |
| | | 5 | 97 |
| | | 1 | 50 |

Coxsackie B$_3$, Vero Cells; 100 TCID$_{50}$

| Cytotoxicity | | Concentration | |
|---|---|---|---|
| CTD$_{50}$ (μ/ml) | CTD$_0$ (μg/ml) | Of Compound (μg/ml) | % Inhibition |
| 33 | 10 | 50 | 100 |
| | | 10 | 100 |
| | | 5 | 100 |
| | | 1 | 75 |

Polio I, Vero Cells; 316 TCID$_{50}$

| Cytotoxicity | | Concentration | |
|---|---|---|---|
| CTD$_{50}$ (μg/ml) | CTD$_0$ (μg/ml) | of Compound (μg/ml) | % Inhibition |
| 33 | 10 | 50 | 100 |
| | | 10 | 100 |
| | | 5 | 100 |
| | | 1 | 100 |

Polio I, Vero Cells; 56.2 TCID$_{50}$

| Cytotoxicity | | Concentration | |
|---|---|---|---|
| CTD$_{50}$ (μg/ml) | CTD$_0$ (μg/ml) | Of Compound (μg/ml) | % Inhibition |
| 33 | 10 | 50 | 100 |
| | | 10 | 100 |
| | | 5 | 100 |
| | | 1 | 86 |

CYTOTOXICITY OF ACETYLATED 5-(3',4'-DIMETHOXYBENZAL) HYDANTOIN AGAINST VERO CELLS AND PRIMARY MONKEY KIDNEY CELLS

| Concentration in micrograms/ml | Toxicity (%) | |
|---|---|---|
| | Vero | pMK |
| 300 | 100 | 100 |
| 250 | 75 | 100 |
| 200 | 25 | 75 |
| 150 | 10 | 10 |
| 100 | 10 | 0 |
| 75 | 10 | 0 |
| 66.7 | 10 | 0 |
| 50 | 10 | 0 |
| 33.3 | 10 | 0 |
| 25 | 10 | 0 |
| 10 | 10 | 0 |
| 6.7 | 0 | 0 |
| 3.3 | 0 | 0 |

| Concentration | Toxicity (%) | |
|---|---|---|
| in micrograms/ml | Vero | pMK |
| 1.0 | 0 | 0 |
| 0.7 | 0 | 0 |
| 0.3 | 0 | 0 |
| 0.1 | 0 | 0 |

When acetylated 5-(3',4'-dimethoxybenzal) hydantoin (Example 14) was injected intraperitoneally into mice the subacute $LD_{50}$ during 16 days by daily injection was 400–500 mg/kg. Oral administration showed an $LD_{50}$ of greater than 1,300 mg/kg in mice.

Acetylated 5-(3',4'-dimethoxybenzal) hydantoin (Example 14) was tested in Cynomolgus monkeys, weighing from 2-4 kg, that were infected with the Mahoney strain of Polio virus, at a dosage of 25 mg/kg per day initially for six days by the intraperitoneal route and thereafter subcutaneously for an additional 8 days. The compound was administered in a 0.5% saline solution containing a small amount of dimethylsulfoxide and emulsifier. The solution was subjected to ultrasonic irradiation in order to disintegrate and disperse the compound throughout the solution.

The results obtained in the monkey tests and set forth in the table below indicated that acetylated 5-(3',4',dimethoxybenzal) hydantoin was effective against the Mahoney Polio virus strain in the infected animals.

ACETYLATED 5-(3'4'-DIMETHOXYBENZAL) HYDANTOINS
25 mg/kg/day, i.p. or s.c.
Poliovirus 2 (Mahoney), $TCID_{50}10^{7.8}$ Cyanomolgus Monkey
CUMULATIVE MORBIDITY

| Group | Treatment | PARALYSES | | | PRESENCE OF POLIOVIRUS IN RECTAL SWABS | | | | | | | | HISTOPATHALOGICAL CHANGES AS BRAIN | |
|---|---|---|---|---|---|---|---|---|---|---|---|---|---|---|
| | | No. | % | Average Day of Paralysis | 4th Day | | 8th Day | | 11th Day | | 15th Day | | | |
| | | | | | No. | % | No. | % | No. | % | No. | % | No. | % |
| I | Virus + substance | 2/8 | 25.0 | 13.5 | 4/11 | 36.4 | 2/8 | 25.0 | 2/8 | 25.0 | 1/6 | 16.7 | 2/10 | 20.0 |
| II | Virus, only | 4/11 | 36.4 | 11.0 | 10/12 | 83.3 | 6/8 | 75.0 | 4/9 | 44.4 | 2/5 | 40.0 | 5/11 | 54.5 |
| III | substance only | 0/5 | 0 | — | 0/5 | 0 | 0/5 | 0 | 0/5 | 0 | 0/3 | 0 | 0/5 | 0 |

The compounds of the present invention formulated with a suitable liquid or solid carrier can be used to control, i.e., treat or prevent, viral infection in vertebrates. Sterile liquid carriers may be employed where appropriate. The routes of administration include intranasal, oral and parenteral administration. The first mode of administration can be conveniently effected by means of aerosol formulations employing the widely-known and used propellants in a suitable dispenser. An injectible composition or formulation may comprise a suspension or solution of the active compound in a mixture of normal saline solution and a pharmaceutically acceptable solvent, at a concentration of from about 0.05 to 0.10%.

Oral administration may be in the form of tablets, pills, capsules, granules, powders, syrups and the like.

Suitable pharmaceutically acceptable solid carriers include starches, sugars, various stearates and carbonates, kaolin, talc, dicalcium phosphate, calcium sulfate, and gums. Pharmaceutically acceptable liquid carriers include water oils and water-oil emulsions which advantageously include suitable dispersing or suspending agents such as tragacanth, alginates, dextran, methyl cellulose, polyvinylpyrrolidone, gelatin, and mixtures thereof. Suitable oils for solutions and water-oil emulsions include vegetable oils such as cottonseed oil, coconut oil, peanut oil and the like. For injectible solutions the liquid carrier, e.g. normal saline, may include a solubilizer, such as N,N-dimethylacetamide or N,N-dimethylformamide.

The compounds are administered in effective, but non-toxic dosages, for example, about 1 to 500 mg per kg of body weight per day, preferably about 1–100 mg/kg per day administered in one dose or in a series of doses. A dosage unit may comprise from about 1 to 500 mg. of the compound.

The following examples are provided to describe the present invention in greater detail; however, they should not be construed to be limitations thereof. The melting points are in °C.

EXAMPLE 1

5-(3',4'-Dihydroxybenzal) hydantoin

A mixture of 3,4-dihydroxybenzaldehyde (2.072 g.) and hydantoin (1.50 g.) in water (15 ml) was heated to 70° to give a clear solution. To this was added monoethanolamine (1.38 g.) and the magnetically stirred mixture was heated (90°–92°, bath temperature) for 4 hours. Within 10 minutes crystallization occurred. The product was allowed to cool to room temperature and was stored overnight. After immersing in an ice-bath, the mixture was acidified with ECl, refrigerated 5 hours, filtered, washed with cold (−10°) 1:1 methanol-water and dried. The title compound was obtained as a pale brown solid: 2.776 g, m.p. 300°–310°. (Trituration with hot absolute ethanol gave a pale brown solid in ca 65% recovery, m.p. 320° decomp.)

EXAMPLE 2

5-(3'-Methoxy-4'-Hydroxybenzal) hydantoin

Vanillin (3.04 g.) and hydantoin (2.0 g.) in water (20 ml were heated on the steam-bath for a few minutes until dissolution occurred. Ethanolamine (0174 g.) was then added and the solution heated at 85°–90° (bath temperature) for 4.5 hours. The solution deposited crystals and solidified within 0.5 hours. Concentrated HCl (5 ml) was added, the mixture was refrigerated overnight (18 hours), filtered, water washed and dried. The title compound was obtained as a yellow solid (4.18 g; 93%), m.p. 266°–271° decomp.

A portion (4.122 g.) was crystallized from aqueous ethanol at −10° overnight. Weight of yellow solid: 3.420 g., m.p. 267°–271°. (T. B. Johnson and R. Bengis, J. Amer. Chem. Soc., 35, 1611 (1913) give m.p. 264°–265°.)

EXAMPLE 3

5-(2'-Chlorobenzal) hydantoin

A mixture of o-chlorobenzaldehyde (2.50 g.) and hydantoin (1.78 g., 1 molar ratio) was treated with water (15 ml) and heated to 70°. Monoethanolamine (1.63 g., 1.5 molar ratio) was added and the mixture was stirred magnetically at 90°–92° (bath temperature) for 4.25 hours. The mixture was cooled in an ice-bath, acidified with concentrated HCl, refrigerated overnight, filtered, washed with water and dried at 55°/10 mm. The title compound was obtained as a pinkish solid (2.63 g.), m.p. 266°–270° decomp.

EXAMPLE 4

5-(4'-Nitrobenzal) hydantoin

A mixture of p-nitrobenzaldehyde (2.510 g.) and hydantoin (1.671 g., 1 molar ratio) in water (15 ml) was heated to 70°. Monoethanolamine (1.53 g., 1.5 molar ratio) was added and the mixture was stirred magnetically and heated at 90°–92° (bath temperature) for 4¼ hours. The mixture was cooled in an ice-bath and acidified with HCl. After refrigeration overnight the mixture was filtered, washed with water and dried at 55°/10 mm. The title compound was obtained as a brown solid (3.250 g.), m.p. 252°–253° decomp.

EXAMPLE 5

5-(3',4'-Methylenedioxybenzal) hydantoin

A mixture of 3,4-methylenedioxybenzaldehyde (2.515 g.) and hydantoin (1.668 g., 1 molar ratio) in water (15 ml) was heated to 70° and monoethanolamine (1.40 g., 1.5 molar ratio) was added. This 2 layer liquid mixture was stirred magnetically and heated at 90°–92° (bath temperature) for 4 hours. The title compound was obtained as a pale yellow solid (3.440 g.), m.p. 248°.

Crystallization of the crude material from dioxane gave a colorless solid in 90% yield, m.p. 251°–252°.

EXAMPLE 6

5-(2',5'-Dimethoxybenzal) hydantoin

A mixture of 2,5-dimethoxybenzaldehyde (2.504 g.) and hydantoin (1.507 g., 1 molar ratio) in water (15 ml) was heated to 70°. To this 2 layer liquid was added monoethanolamine (1.38 g., 1.5 molar ratio). The mixture was heated 4 hours at 90°–92° (bath temperature) with magnetic stirring. The title compound was isolated in the usual manner and obtained as a yellow solid (3.288 g.), m.p. 250°–252°. Crystallization from dioxane (96% recovery) gave m.p. 251°–252°.

EXAMPLE 7

5-(3',5'-Dimethoxybenzal) hydantoin

A mixture of 3,5-dimethoxybenzaldehyde (2.550 g.) and hydantoin (1.505 g., 1 molar ratio) in water (15 ml) was heated to 70°. Monoethanolamine (1.38 g., 1.5 molar ratio) was added and the 2 layer liquid mixture was magnetically stirred at 90°–92° (bath temperature) for 4 hours. Isolation in the usual manner gave the title compound as a beige solid (2.870 g.), m.p. 285°–287°.

EXAMPLE 8

5-(2',4',5'-Trimethoxybenzal) hydantoin

A mixture of 2,4,5-trimethoxybenzaldehyde (2.503 g.) and hydantoin (1.275 g., 1 molar ratio) in water (15 ml) was heated to 70°. Monoethanolamine (1.17 g.) was added and the suspension was stirred and heated at 90°–92° (bath temperature) for 4 hours. Isolation in the usual manner gave the title compound as a yellow solid (3.305 g.), m.p. 276°–277° decomp. Crystallization from dioxane did not raise the melting point.

EXAMPLE 9

5-(3',4'5'-Trimethoxybenzal) hydantoin

A mixture of 3,4,5-trimethoxybenzaldehyde (2.497 g.) and hydantoin (1.276 g., 1 molar ratio) in water (15 ml) was heated to 70°. Monoethanolamine (1.17 g., 1.5 molar ratio) was added, followed by magnetic stirring and heating (90°–92°, bath temperature) for 4 hours. Usual workup gave the title compound as a yellow solid (2.950 g.), m.p. 266°–268°. Crystallization from dioxane (80% recovery) gave m.p. 268°–270°.

EXAMPLE 10

5-(2'-Methoxybenzal) hydantoin

A mixture of o-methoxybenzaldehyde (2.00 g., 14.7 mmoles) and hydantoin (1.47 g., 1 molar ratio) in water (12 ml) was heated to 70°; monoethanolamine (1.35 g., 1.5 molar ratio) was then added. The mixture was heated in an oil bath (90°–92°) and stirred magnetically for 4 hours. Usual workup gave the title compound as an orange solid (2.90 g.), m.p. 174°–179°.

EXAMPLE 11

5-(3'-Methoxybenzal) hydantoin

A mixture of m-methoxybenzaldehyde (2.00 g., 14.7 mmoles) and hydantoin (1.47 g.) in water (12 ml) was heated to 70°; monoethanolamine (1.35 g., 1.5 molar ratio) was then added and the mixture was heated in an oil bath at 90°–92° for 4 hours with magnetic stirring. Isolation in the usual manner gave the title compound as a beige solid (2.56 g.), m.p. 229°–231°.

EXAMPLE 12

5-(4'-Methoxybenzal) hydantoin

A mixture of p-methoxybenzaldehyde (2.00 g., 14.7 mmoles) and hydantoin (1.47 g., 1 molar ratio) in water (12 ml) was heated to 70°; monoethanolamine (1.35 g., 1.5 molar ratio) was then added. The mixture was stirred magnetically and heated in an oil bath at 90°–92° for 4 hours. Usual workup furnished the title compound as a pale yellow solid (2.74 g.), m.p. 250°–252°.

EXAMPLE 13

5-(3',4'-Dimethoxybenzal) hydantoin

A magnetically stirred mixture of veratraldehyde (9.00 g., 93% pure), hydantoin (5.00 g.), fused, anhydrous sodium acetate (10 g.) and glacial acetic acid (20 ml) was refluxed (bath temperature 160°–165°) for 1.5 hours (solution within 5 minutes, crystallization during heating period). On cooling, water was added. The mixture was stirred for 1 hour, refrigerated 2 hours, filtered, washed with water and dried overnight at 55°/10 mm. The title compound was obtained as a yellow solid: 4.72 g. (38% yield) m.p. 280°–282°.

EXAMPLE 14

Acetylated 5-(3',4'-Dimethoxybenzal) hydantoin

A mixture of pure 3,4-dimethoxybenzaldehyde (4.20 g; 99.9% pure by vpc), hydantoin (2.80 g.), potassium bicarbonate (3.20 g.) and acetic anhydride (10 ml) was stirred magnetically and heated in an oil-bath at 130°-140° (bath temperature) for 30 minutes. After allowing the solution to stand overnight (during which time crystallization occurred) water (100 ml) was added, over 30 minutes, with stirring. The product was isolated by filtration, washed with hot water (250 ml) and dried overnight at 50°/10 mm. Wt. of yellow solid: 3.90 g., m.p. 183°-218°. Acetyl value: 15.5 (theoretical for monoacetylation is 14.8).

A similar result was obtained when fused anhydrous sodium acetate was used in place of potassium bicarbonate.

EXAMPLE 15

Acetylated 5-(3'-methoxy-4'-acetoxybenzal) hydantoin

A mixture of vanillin (1.900 g.), hydantoin (1.4 g.) and fused anhydrous sodium acetate (1.3 g.) in acetic anhydride (5 ml) was heated under a reflux condenser at 125°-130° (bath temperature) with magnetic stirring for 30 minutes. On standing overnight, the solution solidified completely. Water (50 ml) was added and the mixture was stirred at room temperature for about one hour, then refrigerated 5 hours, filtered, washed with boiling water (ca. 200 ml) and dried at 50°/10 mm overnight (18 hours). The crude title compound was obtained as yellow solid: 2.950 g. (86% yield) m.p. 188°-191°.

EXAMPLE 16

Acetylated 5-benzalhydantoin

A magnetically stirred mixture of benzaldehyde (2.60 g.), hydantoin (2.80 g.), fused anhydrous sodium acetate (2.60 g.) and acetic anhydride (10 ml) was heated at 125°-135° (bath temperature) under a reflux condenser for 30 minutes. Dissolution and crystallization occurred during this time. On gradual cooling to room temperature (1.5 hours), water was added, the mixture was refrigerated overnight (18 hours), filtered, washed with hot water (150 ml) and with light petroleum ether. The product was dried 50°/10 mm for 24 hours. The title compound was obtained as a beige solid: 4.76 g., m.p. 214°-217°.

EXAMPLE 17

Acetylated 5-(2'-methoxybenzal) hydantoin

A mixture of o-methoxybenzaldehyde (2.58 g.), hydantoin (1.95 g.), fused, anhydrous sodium acetate (1.95 g.) and acetic anhydride (7.5 ml) was stirred magnetically and heated in an oil bath at (125°-130°) for 30 minutes (solution after 2 minutes). The mixture was removed from the bath and kept at room temperature (crystallization on cooling overnight). Water was then added, followed by refrigeration for 6 hours. The crystals were filtered off, washed with hot water and dried at 55°/10 mm. the title compound was obtained as a yellow solid (3.80 g.).

EXAMPLE 18

Acetylated 5-(3'-methoxybenzal) hydantoin

A mixture of m-methoxybenzaldehyde (2.58 g.), hydantoin (1.95 g.), fused, anhydrous sodium acetate (1.95 g.) and acetic anhydride (7.5 ml) was stirred magnetically and heated in an oil bath at 125°-130° for 30 minutes, (solution within 10 minutes, crystallization on cooling). The mixture was kept at room temperature overnight, treated with water, refrigerated 6 hours, filtered, washed with hot water and dried. The title compound was obtained as a pale yellow solid (4.12 g.).

EXAMPLE 19

Acetylated 5-(4'-methoxybenzal) hydantoin

A mixture of p-methoxybenzaldehyde (2.58 g.), hydantoin (1.95 g.), fused, anhydrous sodium acetate (1.95 g.) and acetic anhydride (7.5 ml) was stirred magnetically and heated in an oil bath at 125°-130° for 30 minutes. The mixture was stored at room temperature overnight, treated with water, refrigerated for 6 hours, filtered, washed with hot water and dried. The title compound was obtained as a pale yellow solid (3.61 g.) m.p. 218°-223° decomp.

EXAMPLE 20

Acetylated 5-(2',5'-dimethoxybenzal) hydantoin

A mixture of 2,5-dimethoxybenzaldehyde (2.10 g.), hydantoin (1.40 g.) and fused, anhydrous sodium acetate (1.30 g.) in acetic anhydride (5 ml) was heated at 125°-130° (bath temperature for 30 minutes with magnetic stirring (solution within 10 minutes). During overnight standing at room temperature, solidification occurred. Water (15-20 ml) was used and the mixture was stirred 1-1.5 hours. More water (60-70 ml) was added followed by refrigeration overnight. The product was filtered, washed with hot water (ca. 150 ml). The title compound was obtained as a tacky solid (3.35 g.).

The crude material (2.893 g.) was crystallized from acetic acid to give a yellow solid (1.977 g.).

EXAMPLE 21

Acetylated 5-(3',5'-dimethoxybenzal) hydantoin

A mixture of 3,5-dimethoxybenzaldehyde (2.10 g.), hydantoin (1.40 g.) and fused, anhydrous sodium acetate (1.30 g.) in acetic anhydride (5 ml) was heated, with magnetic stirring, at 125°-130° (bath temperature) for 30 minutes. After standing at room temperature overnight (crystallization), water (15-20 ml) was added, the mixture was stirred for 1-1.5 hours and then diluted with more water (60-70 ml) followed by refrigeration overnight. The mixture was filtered, washed with water and dried. The title compound was obtained as a pale yellow solid (3.24 g.).

EXAMPLE 22

Acetylated 5-(2',4',5'-trimethoxybenzal) hydantoin

A mixture of 2,4,5-trimethoxybenzaldehyde (2.10 g.), hydantoin (1.40 g.) and fused, anhydrous sodium acetate (1.30 g.) in acetic anhydride (5 ml) was magnetically stirred and heated at 125°-130° (bath temperature) for 30 minutes. During storing at room temperature, solidification took place. Water (15-20 ml) was added, the mixture was stirred 1-1.5 hours, followed by addition of more water (60-70 ml), and refrigeration overnight. The product was filtered, washed with hot water and dried 20 hours, 50°/10 mm. The title compound was obtained as a yellow solid (2.417 g.).

EXAMPLE 23

Acetylated 5-(3',4',5'-trimethoxybenzal) hydantoin

A mixture of 3,4,5-trimethoxybenzaldehyde (2.10 g.), hydantoin (1.40 g.) and fused, anhydrous sodium acetate (1.30 g.) in acetic anhydride (5 ml) was heated at 125°-130° (bath temperature) for 30 minutes with magnetic stirring (solution after 5 minutes). During storage at room temperature overnight solidification took place. Water (15-20 ml) was added, the mixture was stirred 1-1.5 hours, followed by more water addition (60-70 ml). After refrigeration overnight, the crystals were filtered off, washed with hot water (~150 ml) and dried 20 hours, 50°/10 mm. The title compound was obtained as a yellow solid (2.60 g.), m.p. 185°-195°. Crystallization from acetic acid gave the product in 81% yield, m.p. 190°-201°.

EXAMPLE 24

Acetylated 5-(3',4'-methylenedioxybenzal) hydantoin

A mixture of piperonal (2.199 g.), hydantoin (1.60 g.) and fused, anhydrous sodium acetate (1.50 g.) in acetic anhydride (5 ml) was stirred magnetically and heated in an oil bath at 130°±2° (bath temperature) for 30 minutes, (solution and crystallization within 5 minutes). After keeping the product at room temperature for 16 hours, water was added and the mixture was stirred for 0.5 hours followed by addition of more water and refrigeration for 6.5 hours. The mixture was filtered, the residue washed with hot water (150 ml) and dried 20 hours at 50°/10 mm. The title compound was obtained as a yellow solid (3.105 g.), m.p. 260°-262° decomp.

EXAMPLE 25

Acetylated 5-(3',4'-diacetoxybenzal) hydantoin

A mixture of protocatechualdehyde (2.50 g.), hydantoin (2.50 g.) and fused, anhydrous sodium acetate (1.25 g.) in acetic anhydride (12.5 ml) was stirred magnetically and heated at 105°-110° (bath temperature) for 0.75 hours (solution within 10 minutes). Water (12.5 ml) was added to the hot solution and the precipitating mixture was refrigerated overnight, filtered, water washed and dried 5 hours at 55°/10 mm. The title compound was obtained as a colorless solid (1.64 g.), m.p. 200°-210°.

A portion (0.958 g.) of the latter compound was crystallized from acetic acid at room temperature. Weight of colorless solid: 0.703 g., m.p. 233°-239°.

EXAMPLE 26

Acetylated 5-(2'-chlorobenzal) hydantoin

A mixture of o-chlorobenzaldehyde (2.10 g.), hydantoin (1.80 g.) and fused, anhydrous sodium acetate (1.50 g.) in acetic anhydride (5 ml) was heated at 125°-130° (oil bath temperature) for 30 minutes with magnetic stirring (solution after 5 minutes). On cooling to room temperature solidification took place. The mixture was left at room temperature overnight, treated with water (ca. 25 ml), stirred for 1-1.5 hours and refrigerated 5 hours. The solid filtered off, washed with hot water and dried 18 hours at 55°/10 mm. The title compound was obtained as a yellow solid (3.61 g.).

EXAMPLE 27

Acetylated 5-(4'-nitrobenzal) hydantoin

A mixture of p-nitrobenzaldehyde (2.00 g.), hydantoin (1.40 g.) and fused, anhydrous sodium acetate (1.30 g.) in acetic anhydride (5 ml) was stirred magnetically and heated at 125°-130° (bath temperature) for 30 minutes (solution within 5 minutes). On cooling to room temperature solidification took place. The material was left overnight, treated with water (ca. 25 ml) and stirred for 1.5 hours. More water (ca. 75 ml) was added followed by refrigeration for 40 hours. Filtration of the somewhat sticky solid, washing with hot water (ca. 50 ml) and drying at 50°/10 mm over the weekend afforded the title compound as a brown solid (3.59 g.), m.p. >300°.

EXAMPLE 28

Propionylated 5-(3',4'-dimethoxybenzal) hydantoin

A mixture of pure veratraldehyde (2.10 g., 99.9% pure, by VPC), hydantoin (1.40 g.) and potassium bicarbonate (1.60 g.) in propionic anhydride (6 ml) was magnetically stirred and heated in an oil bath at 125°-130° (bath temperature) for 30 minutes (clear solution after 5 minutes, then gradual crystallization). The mixture was then left at room temperature overnight (20 hours). Water was added, followed by magnetic stirring for 45 minutes to decompose residual anhydride. The mixture was refrigerated for 8.5 hours, filtered, washed with hot water (25-35 ml) and dried overnight at 55°/10 mm. The crude title compound was obtained as a yellow solid (3.07 g.). Substantially the same results are obtained when the benzaldehydes described in the preceding examples are similarly treated.

EXAMPLE 29

Mono- and Diacetylation of 5-(3',4'-dimethoxybenzal) hydantoin

A mixture of 5-(3',4'-dimethoxybenzal) hydantoin (1.00 g., m.p. 280°-281°) and acetic anhydride (10 ml) was refluxed at 150°±5° (bath temperature) for 6 hours (crystallization on cooling). The mixture was refrigerated over the weekend, filtered and the solid dried overnight at 50°/10 mm. Weight of yellow solid (0.416 g.), m.p. 204°-208° C. A portion (0.375 g.) of the latter solid was crystallized from glacial acetic acid to give 0.298 g., m.p. 207°-211°. Acetyl value 16.1. (Theoretical for monoacetylation: 14.8%).

The filtrate from the above first crop (0.416 g.) was treated with water (precipitation) and refrigerated. The precipitated solid was filtered and dried at 50°/10 mm. Weight of yellow solid: 0.530 g., m.p. 152°-154°. Crystallization from glacial acetic acid (76% recovery) gave m.p. 150°-155°. Acetyl value: 22.0. (Theoretical for diacetylation: 25.9%).

When the reaction time was extended to 16 hours, similar results were obtained.

EXAMPLE 30

Acetylation of 5-(3',4'-dimethoxybenzal) hydantoin with sodium acetate-acetic anhydride A mixture of 5-(3',4'-dimethoxybenzal) hydantoin (1.04 g.), prepared by sodium hydroxide hydrolysis of product described in Example 14, and fused anhydrous sodium acetate (0.44 g.) in acetic anhydride (6 ml) was heated with magnetic stirring at 125°-130° C. (bath temperature) for about 30 minutes. After storage at room temperature overnight, during which time crystallization had taken place, water was added. Isolation of the product by filtration gave a yellow solid (1.49 g.). The product was crystallized from acetic acid to give a crystalline yellow solid (acetyl value 15.1%). This product is highly effective against Picorna group of viruses.

Substantially the same results are obtained when the 5-(substituted benzal) hydantoins in the preceding examples are similarly treated.

EXAMPLE 31

Preparation of pure N-monoacetylated 5-(3',4'-dimethoxybenzal) hydantoin

Crude N-monoacetylated 5-(3',4'-dimethoxybenzal) hydantoin (110 g.), prepared as described in Example 29, was dissolved in dimethylsulfoxide (180 ml) by heating to 90°. Crystallization occurred on standing overnight. The crystals were filtered off and dried to give 92.8 g. of product. This was recrystallized from dimethylsulfoxide (150 ml) under similar conditions, the crystals were filtered off, washed with ethanol and dried. The product was finely ground, slurried with ethanol (250 ml), filtered, and dried to yield 77.7 g. of the pure monoacetylated derivative, m.p. 223°–225°. N.M.R. showed the presence of one acetyl group per molecule.

EXAMPLE 32

Preparation of pure N,N-diacetylated 5-(3',4'-dimethoxybenzal) hydantoin

The filtrate as obtained in Example 29, containing the N,N-diacetylated 5-(3',4'-dimethoxybenzal) hydantoin, was evaporated to dryness and the residue (128 g.) was dissolved in dimethylacetamide (250 ml) by heating to 100°. Overnight crystallization yielded 69 g. of product which was recrystallized from dimethylacetamide (100 ml) under similar conditions. The dried crystals (55.1 g.) had m.p. 181°–183°. N.M.R. showed the presence of two acetyl groups per molecule.

EXAMPLE 33

Separation of Pure N Mono- and N,N Di-acetylated 5-(3',4'-dimethoxybenzal) hydantoin and isomers The crude reaction product, derived from the acetylation of 5-(3',4'-dimethoxybenzal) hydantoin with fused anhydrous sodium acetate and acetic anhydride as described in Example 30, was crystallized fractionally from dimethylsulfoxide. The fractions than were recrystallized repeatedly from dimethylsulfoxide to yield the following five compounds:

(a) N-Monoacetylated Compound A

This compound had m.p. 254°–256°. N.M.R. showed the presence of one acetyl group per molecule.

(b) N-Monoacetylated Compound B

This compound had m.p. 221°–224°. N.M.R. showed the presence of one acetyl group per molecule.

(c) N-Monoacetylated Compound C

This compound was identical with that described in Example 31.

(d) N,N-Diacetylated Compound D

This compound had m.p. 134°–137°. N.M.R. showed the presence of two acetyl groups per molecule.

(e) N,N-Diacetylated Compound E

This compound was identical with that described in Example 32.

EXAMPLE 34

Preparation of pure N-mono- and N,N-di-acetylated 5-(2',3',5'-Trimethoxybenzal) hydantoin and isomers thereof 5-(2',4',5'-Trimethoxybenzal) hydantoin, prepared as described in Example 8, was acetylated with refluxing acetic anhydride in the manner outlined in Example 29. Fractional crystallization of the crude reaction product from dipolar aprotic solvents such as dimethylsulfoxide and dimethylacetamide provided four purified compounds:

(a) N-monoacetylated Compound A

This compound had m.p. 195°–197° after several recrystallizations from dimethylsulfoxide. N.M.R. showed the presence of one acetyl group per molecule.

(b) N-monoacetylated Compound B

This compound had m.p. 223°–226° after recrystallization from dimethylacetamide. N.M.R. showed the presence of one acetyl group per molecule.

(c) N-N-diacetylated Compound C

This compound had m.p. 187°–189° after crystallizations first from dimethylsulfoxide and then from dimethylacetamide. N.M.R. showed the presence of two acetyl groups per molecule.

(d) N,N-diacetylated Compound D

This compound had m.p. 175°–177° after recrystallization from dimethylacetamide. N.M.R. showed the presence of two acetyl groups in this molecule.

EXAMPLE 35

Acetylation of 5-(3',4'-Dimethoxybenzal) hydantoin in Dimethylacetamide-Pyridine A solution of the above mentioned hydantoin (0.5 g.) in anhydrous dimethylacetamide (5 ml) and anhydrous pyridine (0.6 ml) was treated with acetyl chloride (0.5 ml), when there was immediate precipitation of a yellow solid, with slight evolution of heat. After allowing the mixture to stand at room temperature overnight (17 hours), the product (0.53 g.) m.p. 204°–208° C. was isolated as a yellow solid by precipitation into water. Crystallization from dimethylsulfoxide as described in Example 31 gave yellow crystals (0.170 g.), showing identical N.M.R. spectrum to that of the monoacetylated 5-(3',4'-dimethoxybenzal) hydantoin described in Example 31.

EXAMPLE 36

Pivaloylation of 5-(3',4'-Dimethoxybenzal hydantoin

To a solution of the hydantoin (0.5 g.) in dimethylacetamide (5 ml) and anhydrous pyridine (2 ml), pivaloyl chloride (2 ml) was added and the resultant pale yellow solution left at room temperature over the weekend (67 hours). The solution was poured into water, extracted with methylene chloride and the methylene chloride extract washed once with $NaHCO_3$ solution, then with dilute hydrochloric acid and finally with water. Evaporation of the dried ($Na_2SO_4$) extract left a yellow solid (0.5 g.), m.p. 153°–158°. Crystallization from methylene chloride-light petroleum (bp 30°–60° C.) gave the mono-pivalylated derivative as yellow crystals (0.27 g.), m.p. 177°–178°.

EXAMPLE 37

Palmitoylation of 5-(3',4'-Dimethoxybenzal) hydantoin

To a solution of the above mentioned hydantoin (0.5 g) in dry dimethylacetamide (5 ml) and anhydrous pyridine (1.0 ml) palmitoyl chloride (2.75 g) was added, resulting in formation of a yellow precipitate. After allowing the mixture to stand at room temperature for 64 hours water was added and the resultant solid was filtered off and washed first with water and then repeatedly with hexane. The resulting beige solid (1.5 g), m.p. 75°-78° was crystallized from a mixture of chloroform and light petroleum to give the dipalmitoylated derivative as a nearly colorless solid (0.9 g) m.p. 87°-88°.

The term "vertebrate" as used herein is intended to include mammals and birds, both of which are subject to infection with viruses of the Picorna group.

We claim:

1. A therapeutic composition in dosage unit form comprising a solid or sterile liquid pharmaceutical carrier and from about 1 to 500 milligrams of a compound of the formula:

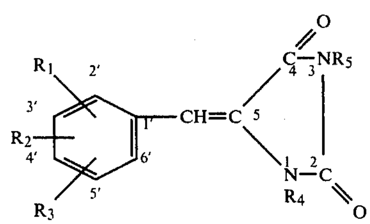

I wherein:

Formula I includes individual geometrical isomers and mixtures thereof, $R_1$, $R_2$ and $R_3$ are each hydrogen, hydroxy, alkoxy of 1 to 4 carbon atoms or alkanoyloxy of 1 to 4 carbon atoms, halo, or nitro, or $R_2$ and $R_3$ together form $—OCH_2O—$; and one of $R_4$ and $R_5$ is alkanoyl containing from 1 to 20 carbon atoms and the other is hydrogen or alkanoyl containing from 1 to 20 carbon atoms.

2. The therapeutic composition of claim 1 wherein at least one of $R_4$ and $R_5$ is acetyl.

3. The therapeutic composition of claim 1 wherein at least one of $R_4$ and $R_5$ is propionyl.

4. The therapeutic composition of claim 1 wherein at least one of $R_4$ and $R_5$ is pivalyl.

5. The therapeutic composition of claim 1 wherein both $R_4$ and $R_5$ are alkanoyl.

6. The therapeutic composition of claim 1 wherein both $R_4$ and $R_5$ are acetyl groups.

7. The therapeutic composition of claim 1 wherein the compound is in solution or suspension in a sterile liquid carrier in a concentration of from about 0.05 to 0.1% by weight.

8. The composition of claim 1 in which the compound of the formula I is acetylated 5-(3'-methoxy-4'-acetoxybenzal) hydantoin.

9. The composition of claim 1 in which the compound of the formula I is acetylated 5-(3',4'-methylenedioxybenzal) hydantoin.

10. A method of treating virus infections caused by enters and foot and mouth disease viruses of the Picorna group which comprises administering to a vertebrate in need of such treatment a non-toxic amount effective to treat viruses of said group of a compound of the formula:

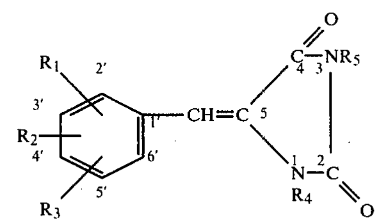

I wherein:

Formula I includes individual geometrical isomers and mixtures thereof, $R_1$, $R_2$, and $R_3$ are each hydrogen, hydroxy, alkoxy of 1 to 4 carbon atoms, alkanoyloxy of 1 to 4 carbon atoms, halo, or nitro, or $R_2$ and $R_3$ together form $—OCH_2O—$;

and one of $R_4$ and $R_5$ is alkanoyl containing from 1 to 20 carbon atoms and the other is hydrogen or alkanoyl containing from 1 to 20 carbon atoms.

11. The method of claim 10 wherein $R_4$ and $R_5$ of the compound are both acetyl groups.

12. The method of claim 10 wherein at least one of $R_4$ and $R_5$ is acetyl.

13. A method of claim 10 wherein at least one of $R_4$ and $R_5$ is propionyl.

14. A method of claim 10 wherein at least one of $R_4$ and $R_5$ is pivalyl.

15. The method of claim 10 in which the compound of the formula I is acetylated 5-(3'-methoxy-4'-acetoxybenzal) hydantoin.

16. The method of claim 10 in which the compound of the formula I is acetylated 5-(3',4'-methylenedioxybenzal) hydantoin.

* * * * *

UNITED STATES PATENT AND TRADEMARK OFFICE
CERTIFICATE OF CORRECTION

PATENT NO. : 4,264,617
DATED : April 28, 1981
INVENTOR(S) : Kekhusroo R. Bharucha et al It is certified that error appears in the above—identified patent and that said Letters Patent is hereby corrected as shown below:

IN THE ABSTRACT:

Line 7 (4th line after the formula), delete "—OCH—" and insert therefor -- —OCH$_2$O— --;

Line 8 (5th line after the formula), delete "$_2$O".

IN THE CLAIMS:

Column 22, line 14 (Claim 10, second line), delete "enters" and insert therefor -- entero --.

Signed and Sealed this

Eighteenth Day of August 1981

[SEAL]

Attest:

GERALD J. MOSSINGHOFF

*Attesting Officer*     *Commissioner of Patents and Trademarks*